US010463275B2

(12) United States Patent
King-Smith

(10) Patent No.: US 10,463,275 B2
(45) Date of Patent: Nov. 5, 2019

(54) DEVICE FOR CAPTURING AND CONCENTRATING VOLATILE ORGANIC COMPOUNDS

(71) Applicant: Elemental Sensor LLC, Aptos, CA (US)

(72) Inventor: Oliver P. King-Smith, Aptos, CA (US)

(73) Assignee: Elemental Sensor LLC, Aptos, CA (US)

( * ) Notice: Subject to any disclaimer, the term of this patent is extended or adjusted under 35 U.S.C. 154(b) by 130 days.

(21) Appl. No.: 15/232,547

(22) Filed: Aug. 9, 2016

(65) Prior Publication Data
US 2017/0035326 A1    Feb. 9, 2017

Related U.S. Application Data

(60) Provisional application No. 62/202,862, filed on Aug. 9, 2015.

(51) Int. Cl.
*A61B 5/08* (2006.01)
*A61B 5/097* (2006.01)
(Continued)

(52) U.S. Cl.
CPC .............. *A61B 5/097* (2013.01); *A61B 5/082* (2013.01); *A61B 5/4082* (2013.01);
(Continued)

(58) Field of Classification Search
CPC ......... G01N 33/497; G01N 2033/4975; A61M 2230/43; A61M 2205/3303; A61B 5/097;
(Continued)

(56) References Cited

U.S. PATENT DOCUMENTS 2,824,789 A    2/1958   Borkenstein
3,552,930 A    1/1971   Borkenstein
(Continued)

OTHER PUBLICATIONS

Heintz et al., Activity Coefficients at Infinite Dilution and Enthalpies of Solution of Methanol, 1-butanol, and 1-hexanol in 1-hexyl-3-methyl-imidazolium bis(trifluoromethyl-sulfonyl) imide, The Journal of Chemical Thermodynamics 39:268-274 (2007).
(Continued)

*Primary Examiner* — Navin Natnithithadha
*Assistant Examiner* — Andrey Shostak
(74) *Attorney, Agent, or Firm* — Karen Canaan; CanaanLaw, P.C.

(57) ABSTRACT

A device for capturing and concentrating volatile organic compounds (VOCs) in a sample of breath air. The device includes an intake for accepting an air sample; a disposable mouth piece; a sensor array for measuring physical parameters of the air sample; an exhaled air sampler for capturing a pre-determined volume of air; a concentrator for concentrating VOCs in the air sample; and an ionic liquid collector, the latter of which may be removed from the device. The ionic liquid collector, which may have one compartment or multiple compartments, includes at least one ionic liquid. Analysis of VOCs in the ionic liquid or liquids may identify biomarkers that can provide a medical diagnosis for a human patient based on a sample of breath air.

44 Claims, 7 Drawing Sheets

(51) Int. Cl.
  *A61B 5/00* (2006.01)
  *A61B 10/00* (2006.01)
  *G01N 33/497* (2006.01)

(52) U.S. Cl.
  CPC ............ *A61B 5/4088* (2013.01); *A61B 5/425* (2013.01); *A61B 5/4216* (2013.01); *A61B 5/4255* (2013.01); *A61B 5/4381* (2013.01); *A61B 10/0041* (2013.01); *G01N 33/497* (2013.01); *A61B 2010/0087* (2013.01); *A61M 2205/3303* (2013.01); *A61M 2230/43* (2013.01); *G01N 2033/4975* (2013.01)

(58) Field of Classification Search
  CPC ... A61B 5/4216; A61B 5/4381; A61B 5/4255; A61B 5/425; A61B 5/4088; A61B 5/4082; A61B 5/082; A61B 10/0041; A61B 2017/0023; A61B 2010/0087
  See application file for complete search history.

(56) References Cited

U.S. PATENT DOCUMENTS

| | | | | |
|---|---|---|---|---|
| 4,034,743 | A * | 7/1977 | Greenwood | A61B 5/08 600/538 |
| 6,493,638 | B1 * | 12/2002 | McLean | G01N 33/0031 702/22 |
| 2003/0109794 | A1 | 6/2003 | Phillips | A61B 5/097 600/543 |
| 2007/0231918 | A1 * | 10/2007 | Zeng | G01N 29/036 436/141 |
| 2009/0090197 | A1 * | 4/2009 | Finlay | G01N 1/2214 73/863.12 |
| 2010/0255198 | A1 * | 10/2010 | Cleary | C23C 16/4402 427/255.39 |
| 2011/0308297 | A1 * | 12/2011 | Tsuzuki | G01N 33/4972 73/23.3 |
| 2013/0253358 | A1 | 9/2013 | Phillips | |
| 2014/0087134 | A1 * | 3/2014 | Gesford | C09D 175/04 428/141 |
| 2014/0288454 | A1 * | 9/2014 | Paz | A61B 5/4845 600/532 |
| 2015/0009503 | A1 * | 1/2015 | Shimoyama | G01N 21/553 356/445 |
| 2015/0032019 | A1 * | 1/2015 | Acker | A61B 5/082 600/532 |
| 2015/0065901 | A1 * | 3/2015 | Bhatnagar | A61B 5/097 600/532 |
| 2016/0029924 | A1 * | 2/2016 | Leonhardt | G01N 33/497 600/532 |
| 2016/0174875 | A1 * | 6/2016 | Forster | A61B 10/00 600/543 |
| 2016/0193543 | A1 * | 7/2016 | Kim | B01D 7/02 564/308 |

OTHER PUBLICATIONS

Kozlova et al., Activity Coefficients at Infinite Dilution of Hydrocarbons, Alkylbenzenes, and Alcohols in the paramagnetic ionic liquid 1-butyl-3-methyl-imidazolium tetrachloridoferrate(III) using Gas-Liquid Chromatography, The Journal of Chemical Thermodynamics 41:330-333 (2009).

Morgan et al., Diffusivities of Gases in Room-Temperature Ionic Liquids: Data and Correlations Obtained Using a Lag-Time Technique, Industrial and Engineering Chemistry Research 44(13):4815-4823 (2005).

Gonzales-Miquel et al., Selection of Ionic Liquids for Enhancing the Gas Solubility of Volatile Organic Compounds, The Journal of Physical Chemistry B 117:296-306 (2013).

Non-final Office Action dated Jan. 2, 2018, for commonly owned U.S. Appl. No. 15/154,600 entitled "Device for Detecting Volatile Organic Compounds."

Response to the Non-final Office Action dated Jan. 2, 2018, filed on Feb. 22, 2018, in commonly owned U.S. Appl. No. 15/154,600 entitled "Device for Detecting Volatile Organic Compounds."

* cited by examiner

DEVICE FOR CAPTURING AND CONCENTRATING VOLATILE ORGANIC COMPOUNDS

CROSS-REFERENCE TO RELATED APPLICATIONS

This application claims priority under 35 U.S.C. 119(e) to U.S. Provisional Application No. 62/202,862, filed on Aug. 9, 2015, which is incorporated in its entirety herein.

TECHNICAL FIELD

The present invention relates generally to medical devices. More specifically, the present invention relates to a medical device for capturing and concentrating volatile organic compounds (VOCs) from a sample of breath air.

BACKGROUND OF THE INVENTION

Breath has long been known to have valuable biomarkers for spotting early stage lung cancer. Handling breath samples has been logistically difficult, with most tests requiring processing to be done rapidly onsite. While studies have shown that dogs can be trained to smell lung cancer, the concentrations of biomarkers is so low that research has been plagued with inconsistent results, given the existing protocols. Small deviations in the way that samples are handled often leads to erroneous results.

Volatile organic compounds (VOCs) make up the majority of the scents and smells human and animals can sense. While smell has not been formally used in routine medical practice, there are well known scents associated with particular conditions. For example, the smell of death is created by VOCs, in particular putrescine and cadaverine, which are released when cells die. Other VOCs, such as ketones, are exhaled if there is not enough insulin to help the body use sugar for energy. Lung cancer has over 40 known VOCs that researches have shown can indicate lung cancer.

A major challenge in measuring the VOCs in breath is the complexity of the sample. There are over 1,000 known compounds in breath. Trying to separate and measure all these compounds has been a logistical challenge for makers of devices. Simple devices often can only measure a class of compounds, or have unknown specificity and selectivity towards different VOCs.

Devices used in research have suffered from being very complex to use, making them difficult to deploy in a standard clinical environment, or they have been to very expensive to use making them unattractive for a screening test. It is therefore appreciated that there is a need in the art for a small and inexpensive device that can be used to capture biomarkers in the breath.

SUMMARY OF THE INVENTION

The present invention overcomes the need in the art by providing a device for capturing and concentrating volatile organic compounds (VOCs) from a sample of breath air. The present invention has the capability to capture multiple VOCs at different concentrations.

In one embodiment, the present invention comprises a device comprising: (a) an intake for accepting a sample of room air; (b) a disposable mouthpiece for use by a human subject, wherein the human subject breaths in the room air through the disposable mouthpiece and exhales breath back into the disposable mouthpiece; (c) a sensor array comprising one or more sensors for measuring physical parameters in the exhaled breath; (d) an exhaled air sampler for capturing a pre-determined volume of air from the exhaled breath; (e) a concentrator for receiving the pre-determined volume of air from the exhaled air sampler and concentrating VOCs in the pre-determined volume of air; and (f) an ionic liquid collector comprising at least one ionic liquid, wherein the pre-determined volume of air comprising concentrated VOCs are deposited and/or injected from the concentrator into the ionic liquid collector.

In another embodiment, the device further comprises a volatile organic compound (VOC) filter in communication with the intake (a) and the disposable mouthpiece (b) for cleaning the room air by removing VOCs from the room air sample.

In still another embodiment, the device further comprises a fan in communication with the intake (a) and the VOC filter for moving the room air from the intake into the VOC filter. The VOC filter may be selected from the group consisting of activated carbon filters, carbon fibers, coalescing filters, corona discharge, electrostatic filters, metal organic frameworks (MOFs), paper, silica, zeolites, and combinations thereof.

In another embodiment, the device further comprises a one-way valve in communication with the VOC filter and the disposable mouthpiece (b) for moving the room air from the VOC filter into the disposable mouthpiece.

In still another embodiment, the device further comprises a tracer source in communication with the VOC filter and the one-way valve, wherein the tracer source measures lung performance of the human subject. The tracer source may be selected from the group consisting of chlorofluorocarbons (CFCs), hydrochlorofluorocarbons (HCFCs), hydrofluorocarbons (HFCs), helium, sulfur hexafluoride, and combinations thereof.

In another embodiment, the device further comprises a one-way valve in communication with the disposable mouthpiece (b) and the sensor array (c) for moving the exhaled breath from the disposable mouthpiece into the sensor array.

In still another embodiment, the device further comprises a VOC source in communication with the one-way valve and the sensor array.

In a further embodiment, the VOC source may comprise crown ethers, 1,1,1,3,3-pentafluorobutane, or a combination of crown ethers and 1,1,1,3,3-pentafluorobutane.

In another embodiment, the sensors on the sensor array (c) are selected from the group consisting of electrical sensors, electrochemical sensors, optical sensors, ultrasonic sensors, semiconductor sensors, and combinations thereof.

In a further embodiment, the physical parameters measured by the sensors on the sensor array (c) comprise temperature, humidity, pressure, and carbon dioxide ($CO_2$) concentration.

In another embodiment, the device further comprises an exhaust in communication with the exhaled air sampler (d), wherein exhaled air in excess of the pre-determined volume of air is expelled from the exhaled air sampler through the exhaust.

In still another embodiment, the device further comprises a pump in communication with the exhaled air sampler and the exhaust, wherein the pump is capable of cleaning the unit.

In another embodiment, the exhaled air sampler (d) further comprises a piston for collecting the pre-determined volume of air from the sensor array (c) and injecting the pre-determined volume of air into the concentrator (e).

In still another embodiment, the exhaled sampler further comprises a cylinder for housing the piston and a motor for driving the piston.

In a further embodiment, the cylinder comprises a heating element to prevent condensation of the VOCs.

In another embodiment, the exhaled air sampler further comprises a pressure sensor for measuring pressure of the breath exhaled by the human subject into the device.

In still another embodiment, the device further comprises a filter in communication with the exhaled air sampler (d) and the concentrator (e), wherein the filter removes moisture and optionally other compounds from the pre-determined volume of air in the exhaled air sampler prior to the pre-determined volume of air entering into the concentrator.

In a further embodiment, the filter may be selected from the group consisting of zeolites, silica gel, metal organic frameworks (MOFs), plastics, poly(dimethylsiloxane) (PDMS), fiber glass, paper, and combinations thereof.

In another embodiment, the concentrator (e) comprises a VOC ionization source selected from the group consisting of chemical ionization, electrostatic radiation, radioactivity, UV light, and combinations thereof.

In still another embodiment, the ionic liquid collector (f) further comprises a VOC trapping element selected from the group consisting of activated carbon, ceramic, metal organic frameworks (MOFs), organic solvents, plastic polymers, silica, water, zeolites, and combinations thereof.

In a further embodiment, the ionic liquid collector (f) is a removable and/or replaceable part of the device.

In another embodiment, the ionic liquid collector (f) further comprises a sealing mechanism that is automatically opened and closed by the concentrator (f).

In a further embodiment, the ionic liquid collector (f) is capable of being inserted into the concentrator (f).

In another embodiment, the ionic liquid collector (f) is comprised of a needle that is injected into the concentrator (e), wherein the concentrator comprises a sealed septa that the needle can penetrate.

In a further embodiment, the septa is comprised of a material selected from the group consisting of polytetraethylene (PTE), polytetrafluoroethylene (PTFE), silicone, and combinations thereof.

In another embodiment, the concentrator (e) comprises a temperature control unit for keeping the ionic liquid in the ionic liquid collector (f) at an optimal temperature for adsorption of VOCs.

In a further embodiment, the temperature control unit has a temperature in the range of about −50° C. to about 150° C.

In another embodiment, the concentrator (e) comprises a delivery arm and a diffuser, wherein the pre-determined volume of air from the exhaled breath passes from the exhaled air sampler (d) through the diffuser arm to the diffuser where it is deposited in the ionic liquid collector (f).

In a further embodiment, the ionic liquid collector (f) further comprises a temperature sensor.

In another embodiment, the ionic liquid collector (f) further comprises a non-volatile storage device for storing information.

In a further embodiment, the non-volatile storage device comprises an electrically erasable programmable read-only memory (EEPROM) chip.

In another embodiment, the ionic liquid collector (f) can hold a volume of ionic liquid ranging from about 0.03 nL to about 10 mL.

In a further embodiment, the ionic liquid collector (f) comprises a single compartment containing a single ionic liquid.

In another embodiment, the ionic liquid collector (f) comprises multiple compartments, wherein the multiple compartments contain a single ionic liquid.

In a further embodiment, the ionic liquid collector (f) comprises multiple compartments, wherein the multiple compartments contain different ionic liquids.

In another embodiment, the ionic liquid collector (f) is comprised of a collector body comprising the at least one ionic liquid, a collector neck comprising an air-tight sealable lid, and a collector arm comprising a gas reservoir, wherein the gas reservoir allows the ionic liquid to expand and contract.

In a further embodiment, the ionic liquid collector (f) is comprised of a material selected from the group consisting of glass, metal, polytetrafluoroethylene (PTFE), and combinations thereof.

In another embodiment, the device further comprises a battery or power supply for powering the device.

In still another embodiment, the device further comprises a controller, wherein operation of the device is implemented through the controller In a further embodiment, the controller is connected to a display and an input device In another embodiment, the controller comprises a networking interface for sending and receiving data generated by the device to third parties.

In a further embodiment, the device is a single portable unit.

In yet a further embodiment, the at least one ionic liquid is specific for diagnosis of a medical condition selected from the group consisting of lung cancer, breast cancer, prostate cancer, colon cancer, pancreatic cancer, throat cancer, small intestine bacterial overgrowth, gastric ulcers, Parkinson's, Alzheimer's, tuberculosis, autism, and combinations thereof.

Additional features and embodiments of the invention will be provided, without limitation, in the detailed description of the invention that is set forth below.

DETAILED DESCRIPTION OF THE INVENTION

Set forth below is a description of what are currently believed to be preferred embodiments of the claimed invention. Any alternates or modifications in function, purpose, or structure are intended to be covered by the claims of this application. As used in this specification and the appended claims, the singular forms "a," "an," and "the" include plural referents unless the context clearly dictates otherwise. The terms "comprises" and/or "comprising," as used in this specification and the appended claims, specify the presence of stated features, integers, steps, operations, elements, and/or components, but do not preclude the presence or addition of one or more other features, integers, steps, operations, elements, components, and/or groups thereof.

As used herein, the term "ionic liquid" is used to describe a salt that can be homogenous or heterogeneous; composed of cations and anions; and can have ions with more than one charge on a molecule. The positive and negative charges in the ionic liquid are in essentially equal proportions. Within the art to which the invention pertains, ionic liquids with more than one charge per ion are sometimes referred to as di-ionic liquids or tri-ionic liquids. The ionic liquids contemplated under the invention may be may be polymerized. As is known to those of skill in the art, polymerized ionic liquids are referred to as polymeric ionic liquids.

As used herein, the terms "Volatile Organic Compound" and "VOC" are used to describe molecules that contain at least one carbon atom and have a vapor pressure above 0.001 mm Hg at 40° C. and normal atmospheric pressure.

As used herein, the term "communication" and "in communication" is meant to refer to components of the devices described herein that work together, but are not necessarily connected to each other.

Following is a description of the invention that references the figures; it is to be understood that characteristics of the present invention that are described in the discussion of a particular figure are not meant to be limited to that figure, but are intended to apply to all embodiments of the invention, including those embodiments shown in the figures and any additional embodiments that are to be appreciated by those of ordinary skill in the art.

Figure 1:
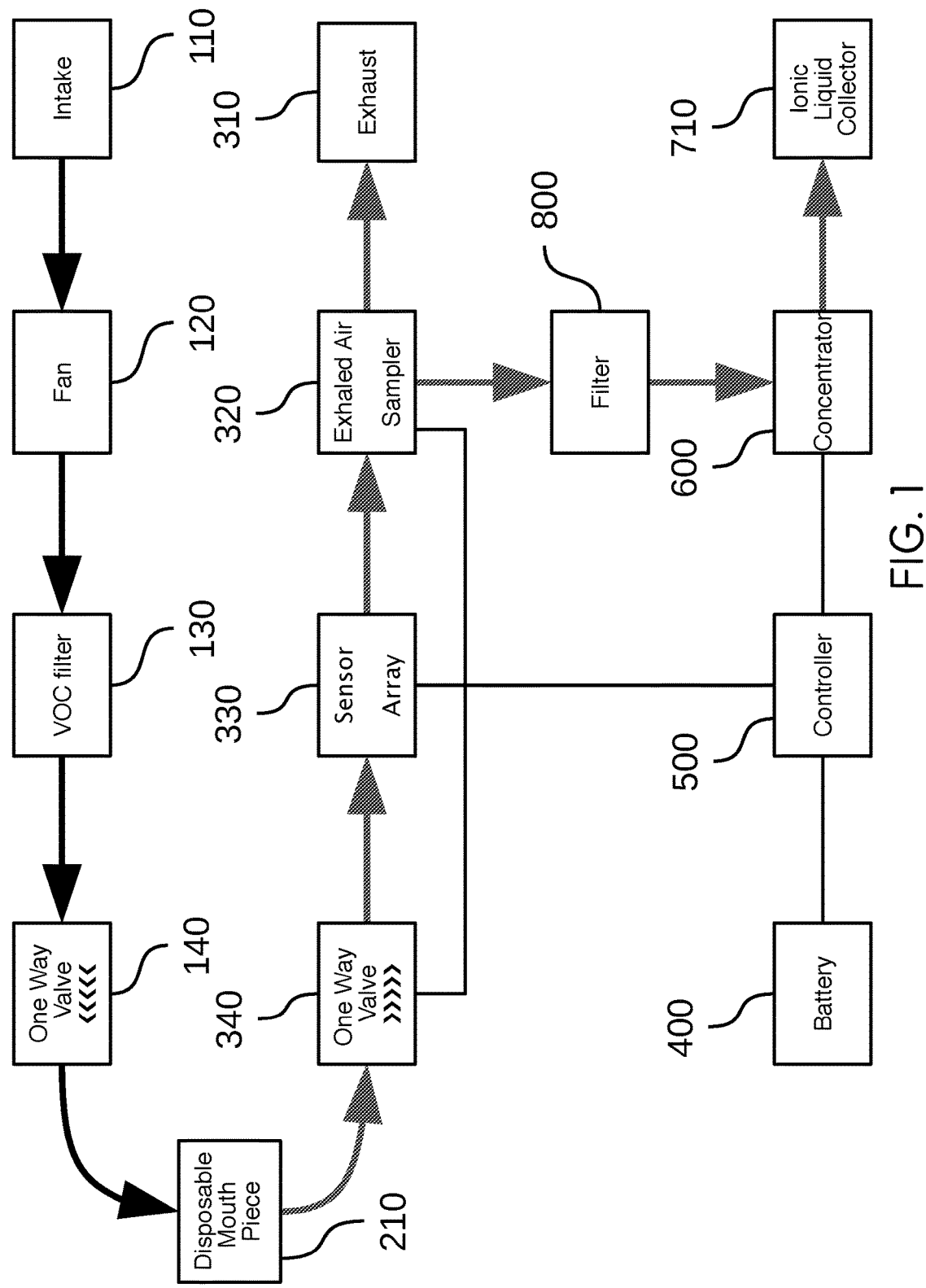
FIG. 1 is a schematic block diagram showing various components of a Breath Capture Device of the present invention.

FIG. 1 shows a schematic block diagram of the Breath Capture Device of the present invention. In application, room air enters the device at the Intake 110 and passes over a Fan 120 towards the VOC filter 130 before going through the One Way Valve 140. The patient breathes in the now cleaned air using a Disposable Mouth Piece 210, and then exhales back through the Disposable Mouth Piece. The exhaled air passes through the One Way Valve 340, over the Sensor Array 330 before being sampled in the Exhaled Air Sampler 320. Exhaled Air not sampled by the Exhaled Air Sampler leaves via the Exhaust 310. The unit is powered by a Battery 400. A Controller 500 is used to coordinate the device's activities. The Exhaled Air Sampler passes the breath sample through an optional Filter 800 before entering the Concentrator 600, which stores the VOCs into a removable Ionic Liquid Collector 710.

In more detail and still referring to FIG. 1, upon entry of room air into the Breath Capture Device, the Breath Capture Device will turn on the Fan 120 to blow the air through the VOC filter 130. The room air will pass through the One Way Valve 140 and into the Disposable Mouth Piece 210. The room air will then leave the Disposable Mouth Piece via the One Way Valve 340 and pass over the Sensor Array 330. The Exhaled Air Sampler 320 will select some of the air to send to the Concentrator 600 and let some of the air flow out of the Exhaust 310. By doing this, the Breath Capture Device has the capability to be self-cleaning. Once the Breath Capture Device has cleaned itself, the Fan 120 can stop or reduce in speed. When the cover on the Disposable Mouth Piece is removed, the patient can now start using the device. The exhaled air from the patient can be monitored by the Sensor Array 330 to determine if the air sample is from the lungs or from the mouth and thorax. Depending on the type of exhaled air desired, the Exhaled Air Sampler 320 will direct a volume of exhaled air through the optional Filter 800 into the Concentrator 600. All these activities are coordinated by the Controller 500. As will be appreciated by those of skill in the art, different air will be of use for different medical indications. For example, Parkinson's, microbiota, neck, throat, mouth, and gastrointestinal (GI) track problems will require the first breath for diagnosis. By contrast, lung cancer, breast cancer, and other non-GI-track cancers will require lung air for diagnosis.

In one embodiment, the Breath Capture Device is designed to be a small portable device, such as for example, a tablet-sized or hand-held sized device.

In another embodiment, the Breath Capture Device is designed to take less than 10 minutes for the Concentrator 600 to store the VOCs into the Ionic Liquid Collector 710.

In a further embodiment, the Ionic Liquid Collector 710 is designed to be replaceable. This allows the sample to be sent to a laboratory for analysis of the captured VOCs. FIGS. 2, 3, 4, 5, and 6 show four representative designs for the Ionic Liquid Collector. It is to be understood that the designs shown in FIGS. 2-6 are illustrative and not meant to be limiting with respect to additional designs for the Ionic Liquid Collector that one of skill in the art would appreciate.

In another embodiment, the Ionic Liquid Collector 710 may have an integrated non-volatile storage mechanism to save information about the breath sample, including without limitation, patient identifiers, atmospheric conditions at the time the sample was taken, time and date of the sample, data from the Sensor Array 330 during operation and cleaning, amount of exhaled air sent to the Concentrator 600, and information about the status of the Breath Capture Device.

In a further embodiment, the Ionic Liquid Collector 710 may be sealed, either before or after being removed from the Concentrator 600.

In another embodiment, the Ionic Liquid Collector 710 may contain other VOC trapping elements other than Ionic Liquids. Examples of other VOC trapping elements that may be used in the Ionic Liquid Collector include without limitation, activated carbon, ceramic, metal organic frameworks (MOFs), plastic polymers, silica, solvents, zeolites, and combinations thereof. Examples of VOC trapping solvents include without limitation, organic solvents, liquid nitrogen, water, and combinations thereof. It is to be understood that this list is not exhaustive and that other materials known to adsorb VOCs may be used with the present invention.

In another embodiment, one or more heaters may be used to assist in the self-cleaning process of the Breath Capture Device. For example, during the self-cleaning process, the Breath Capture Device may use heaters for certain components, such as the Sensor Array 330, the Exhaled Air Sampler 320, and the Concentrator 600, to help ensure all VOCs are removed.

As previously noted, the Breath Capture Device may include an optional Filter 800 for removing moisture. Examples of moisture-removing materials that may be used in the optional Filter include without limitation, zeolites, fiber glass, MOFs, plastics, paper, poly(dimethylsiloxane) (PDMS), silica gel, and combinations thereof. In addition to removing moisture, the Filter may also serve to remove other compounds that might interfere with the VOCs that are being collected. It will be appreciated by those of skill in the art that the preferential blocking of different compounds may be implemented by selecting the appropriate material for the optional Filter. As shown in FIG. 1, the Filter would typically be located between the Exhaled Air Sampler 320 and the Concentrator 600.

Figure 7:
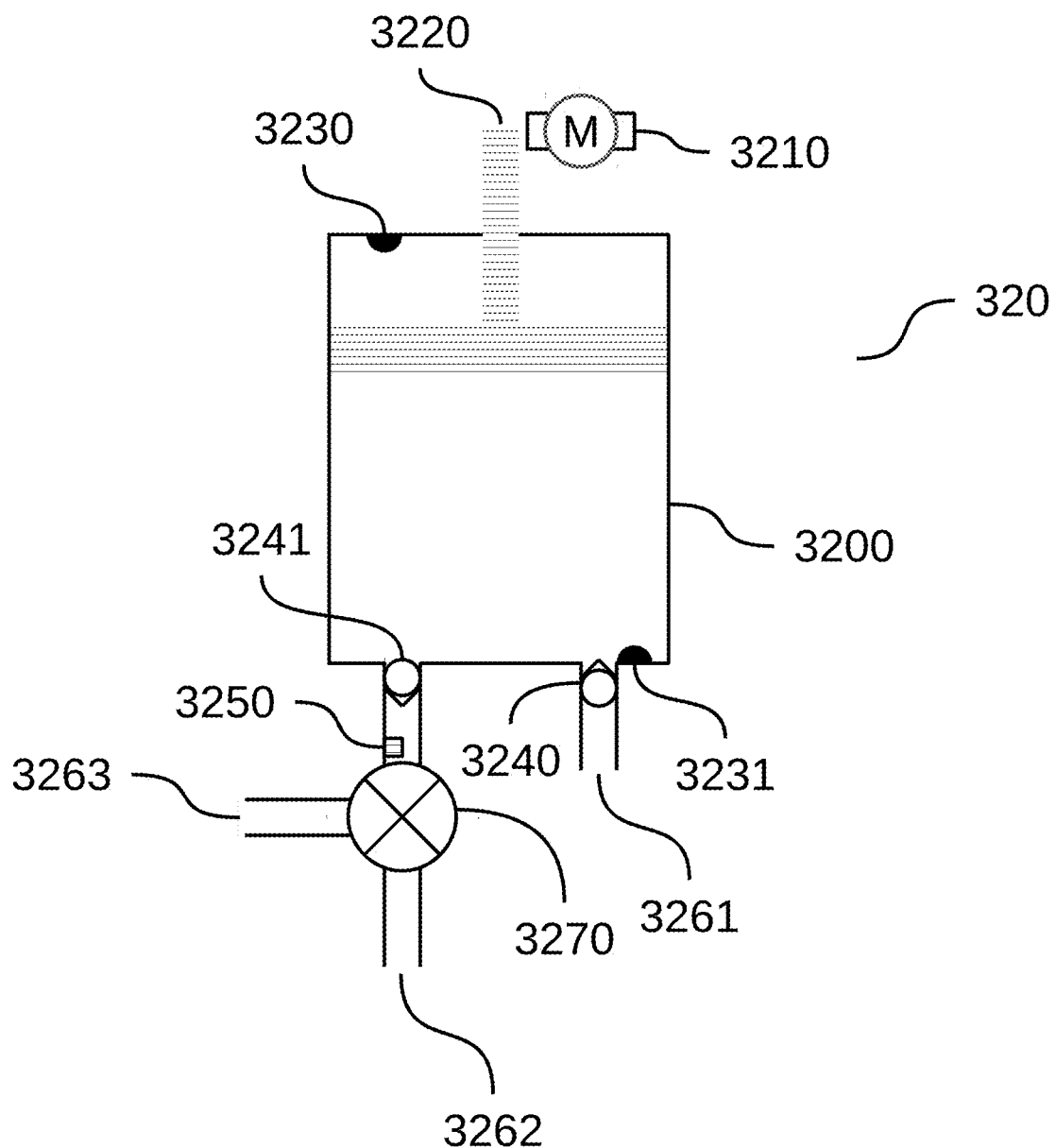
FIG. 7 is a partial sectional view of one embodiment of an Exhaled Air Sampler 320 for a Breath Capture Device of the present invention.

The Exhaled Air Sampler 320 can be implemented in a number of ways known to those of skill in the art. For example, in one embodiment, which is illustrated in FIG. 7, a piston may be used to collect a known volume of air from the exhaled air stream, and then inject it into the Concentrator 600.

The Sensor Array 330 can also be implemented in a number of ways known to those of skill in the art. For example, the Sensor Array may be comprised of any combination of off-the-shelf sensors, such as electrochemical, optical, ultrasonic, and semiconductor sensors. As is shown in FIG. 1, such sensors may be used to measure temperature, humidity, pressure, and $CO_2$ concentration in the breath. As will be appreciated by those of skill in the art, other sensors for measuring various parameters may be substituted for or added to the illustrative sensors referenced herein.

The VOC filter 130 can also be implemented in a number of ways known to those of skill in the art. Examples of filters that may be used to remove the VOCs from the air include without limitation, activated carbon filters, carbon fibers, corona discharge, electrostatic filters, MOFs, paper, zeolites, and combinations thereof. In one embodiment, an optional sensor (not shown) may be included on the VOC filter to make sure that a breakthrough does not occur on the VOC In another embodiment, the Battery 400 can be replaced with a power supply connected to standard mains.

In another embodiment, the Controller 500 can be connected to display(s) and input devices to allow the operator to control the unit. In a further embodiment, the Controller can have networking interfaces for sending and receiving data to the outside world.

Cold surface can cause VOCs to condense inside the unit. It is understood that heating the inside of the unit, to select components between the temperatures of about 20° C. to about 100° C. can reduce or prevent the loss of VOCs on interior surfaces.

In another embodiment, the Disposable Mouth Piece 210 may have a Cover to prevent the air from escaping during the device cleaning. The Cover can also be used to indicate that the Disposable Mouth Piece has not been used. In addition, the Cover can be used to prevent people from touching the surfaces of the Disposable Mouth Piece that the patient will have physical contact with.

In a further embodiment, an optional pump can be added in front of the Exhaust 310 to help clean the unit.

In another embodiment, the Exhaled Air Sampler 320 may send to the Concentrator 600 a sample of the clean air. The Concentrator may process this sample to give a reference measurement of the environment.

In a further embodiment, the Breath Capture Device may contain a VOC Source between the One Way Valve 340 and the Sensor Array 330 or between the Sensor Array 330 and the Exhaled Air Sampler 320. The VOC Source may be used to provide reference sources to check that the system is functioning correctly. Examples of VOC Sources that may be used with the present invention include without limitation, crown ethers, 1,1,1,3,3-pentafluorobutane, other liquid VOCs not found in high concentrations in humans, and combinations thereof.

In another embodiment, the Breath Capture Device may contain a Tracer Source between the VOC Filter 130 and the One Way Valve 140. The Tracer Source can be used to measure lung performance by looking at adsorption of the Tracer Source in the lungs. Examples of Tracer Sources that may be used with the present invention include without limitation, chlorofluorocarbons (CFCs), hydrochlorofluorocarbons (HCFCs), hydrofluorocarbons (HFCs), helium, sulfur hexafluoride, and combinations thereof. As will be appreciated by those of skill in the art, these compounds are safe to breathe and provide a good tracer into the lungs because it can be captured by Ionic Liquids.

Figure 2:
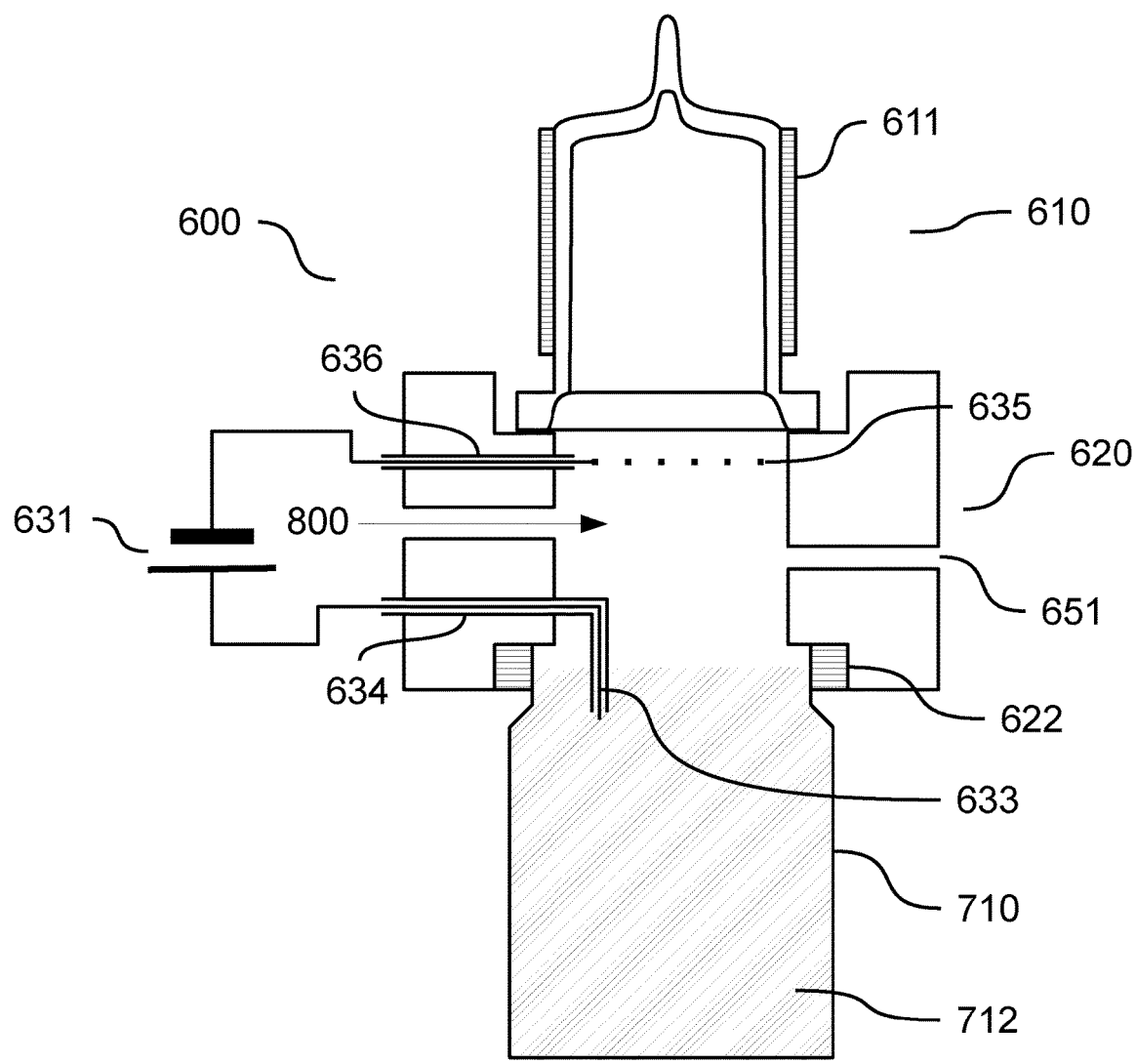
FIG. 2 is a partial sectional view of one embodiment of a Concentrator 600 for a Breath Capture Device of the present invention.

Referring now to FIG. 2, shown is a partial sectional view of one embodiment of the Concentrator 600 of the present invention. The Concentrator is made up of the UV bulb 610 with RF Electrodes 611, which is connected to the Concentrator Walls 620, which in turn allows an Ionic Liquid Collector 710 to be inserted into the bottom of the Concentrator. An Airtight Gasket 622 allows the Ionic Liquid Collector to be inserted and removed from the Concentrator. An electrically Insulated Tube 634 carries a Wire 633 through the Concentrator Walls and a Second Tube 636 carries a second Wire to the Counter Electrode 635. The Counter Electrode and the Wire are biased with a Voltage Source 631.

Still referring to FIG. 2, the Ionic Liquid Collector 710 contains an Ionic Liquid 712. In application, the breath sample 800 enters the Concentrator 600 through the Concentrator Walls 620. Once the breath sample has been used, it is expelled through the Exit Port 651.

In application, the Concentrator 600 works by ionizing the VOCs with the UV bulb 610. The UV bulb is powered by the RF Electrodes 611. As the breath sample 800 enters the Concentrator through an opening in the Chamber Walls 620, the ionized VOCs are subjected to an electric field induced between the Counter Electrode 635 and the Ionic Liquid 712, which moves the ionized VOCs in the electric field towards the Ionic Liquid. As VOCs gather on the surface of the Ionic Liquid, they are adsorbed. It will be appreciated by those of skill in the art that the adsorption of VOCs into the Ionic Liquid can vary depending on temperature; thus, in one embodiment of the invention, the Ionic Liquid Collector 710 may be temperature controlled using heating and/or cooling methods known to those of skill in the art, such as for example, thermoelectrical heating and/or cooling.

Once a breath sample has been concentrated, the Ionic Liquid Collector 710 can be removed and sealed. Like other components of the Breath Capture Device, the Ionic Liquid Collector can be modified to suit different needs. For example, the Ionic Liquid Collector 710 may be equipped with a temperature sensor or a non-volatile storage device, such as EEPROM (electrically erasable programmable read-only memory) chip, for holding information.

In one embodiment, the size of the Concentrator 600 is designed to fit into a portable unit. The UV bulb 610 can vary in size depending on the size and configuration of the hand held unit. In one example, UV bulbs in sizes less than 15 mm in diameter and 30 mm in length, which are commercially available, may be used in the hand held units. The Ionic Liquid Collector 710 can also vary in size depending on the size and configuration of the portable unit. For example, the Ionic Liquid Collector can be designed to hold a volume of liquid ranging from less than 1 μL to over 10 mL. As will be appreciated by those of skill in the art, the different embodiments described herein may be designed to hold different amounts of liquid. For example, the embodiments described herein wherein the Ionic Liquid Collector comprises a large container and/or reservoir, such as for example the designs show in FIGS. 2, 3, 5, and 6 may hold ionic liquids ranging anywhere from about 10 µL to about 10 mL. By contrast, the embodiments wherein the Ionic Liquid Collector comprises a small container, such as for example the design shown in FIG. 4, may hold a very low volume of Ionic Liquid, such as for example, a range of about 0.03 nL to about 0.03 µL of Ionic Liquid. The distance between the UV bulb and the Ionic Liquid 712 can also vary depending on the size and configuration of the portable unit. For example, the distance from between the UV bulb and the Ionic Liquid can vary from 10 cm to less than a few millimeters.

In one embodiment, the UV bulb 610 and the RF Electrodes 611 may be replaced with another method of ionizing VOCs. Examples of methods of ionizing VOCs in air including without limitation, electrostatic radiation, radio-activity, chemical ionization, UV light, and any combination of the foregoing.

In another embodiment, the UV bulb 610 may be replaced with other UV producing light sources, such as for example, LEDs.

In a further embodiment, the Counter Electrode 635 may be removed and the Chamber Walls 620 may be used as the Counter Electrode.

In another embodiment, the design of the Counter Electrode 635 can be varied to achieve the designed performance.

In a further embodiment, a sensor may be used to check and calibrate the performance of the UV bulb 610.

In another embodiment, the Ionic Liquid Collector 710 may have a sealing mechanism that is automatically opened and closed by the Concentrator 600.

In further embodiments, the Ionic Liquid Collector 710 may contain a single compartment containing a single Ionic Liquid 712 or the Ionic Liquid Collector may contain many compartments containing different or similar Ionic Liquids 712.

In a further embodiment, the Voltage Source 631 may be DC or AC. The polarity of the source can vary depending on the designed targets and Ionization Source.

In another embodiment, the Insulated Tube 634 or the Second Tube 636 may be routed through the Intake or Exit Port 651.

Figure 3:
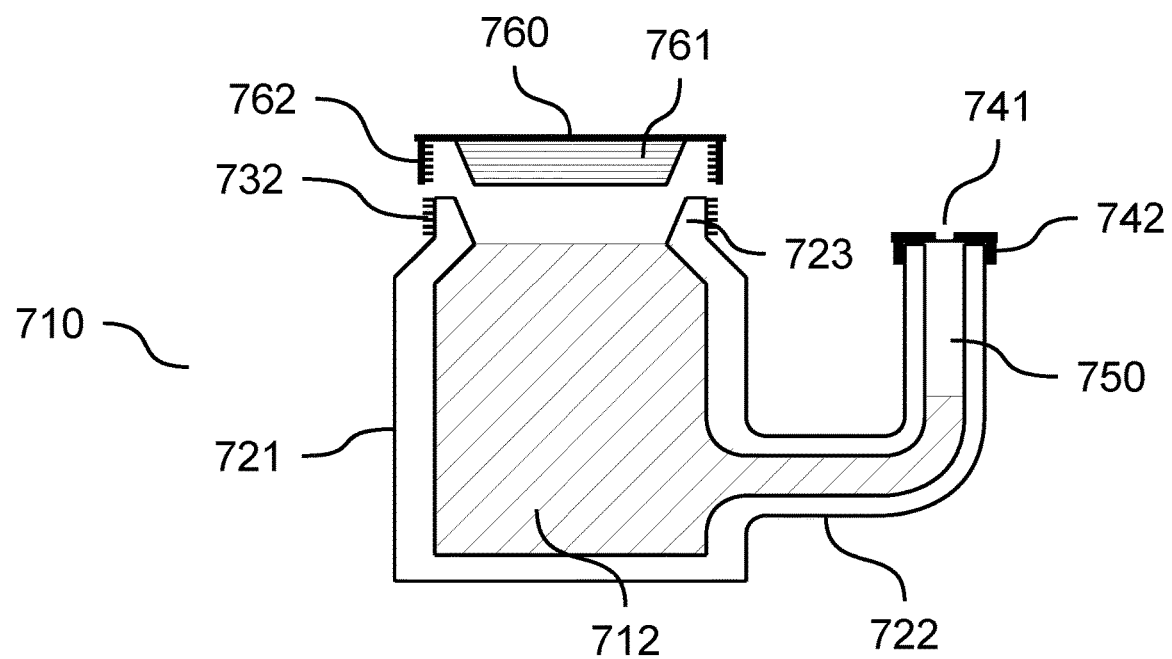
FIG. 3 is a partial sectional view of one embodiment of an Ionic Liquid Collector 710 for a Breath Capture Device of the present invention.

Referring now to FIG. 3, shown is a partial sectional view of one embodiment of the Ionic Liquid Collector 710. The Ionic Liquid Collector is comprised of the Collector Body 721, which is connected to the Collector Arm 722. At the top of the Collector Body is the Collector Neck 723, which has on the outside the Collector Thread 732. At the end of the Collector Arm are the Collector Seal 742 and the Collector Septa 741. A separate Collector Lid 760 is placed on the Collector Body. The Collector Lid has a Lid Thread 762 and a Lid Protrusion 761. The Collector Thread 732, the Collector Lid 762, the Lid Protrusion 761, and Collector Lid 760 comprise a sealing mechanism of the device. Ionic Liquid 712 is held inside the Ionic Liquid Collector. The Collector Arm can contain a Gas Reservoir 750.

Still referring to FIG. 3, as shown therein, the Ionic Liquid Collector 710 holds Ionic Liquid 712. When the Collector Lid 760 is screwed down onto the Ionic Liquid, an air tight connection is made between the Collector Lid and the top of the Collector Neck 723. The shape of the Lid Protrusion 761 is designed to remove most of gas above the Ionic Liquid 712 by fitting snugly in the Collector Neck 723. When the Collector Lid 760 is sealed on top of the Ionic Liquid Collector 710, almost all of the gas in the Ionic Liquid Collector will be contained in the Gas Reservoir 750. The Lid Thread 762 mates with the Collector Thread 732 to hold the Collector Lid in place. When the Ionic Liquid Collector is in use in the Breath Capture Device (not shown), the Collector Thread mates with the Breath Capture Device. During the manufacturing process, the Ionic Liquid Collector is filled with Ionic Liquid 712 under a controlled atmosphere. This process leaves a predetermined amount of known gas in the Gas Reservoir 750. The Ionic Liquid Collector is filled with Ionic Liquid to a height where the Lid Protrusion 761 just touches the top of the Ionic Liquid when the Collector Lid is screwed onto the Ionic Liquid Collector. The Gas Reservoir allows the Ionic Liquid to expand and contract without damaging the Ionic Liquid Collector. Once a breath sample has been collected, a sample can be drawn from the Gas Reservoir by using a needle to puncture through the Collector Septa 741.

The Ionic Liquid Collector 710 can be built out of any material that adsorbs negligible levels of VOCs. Examples of such materials include without limitation, polyfluorotetraethylene (PTFE), glass, metal, and combinations thereof. The Collector Lid 760 can be made of any material that mates well to the Ionic Liquid Collector, such as for example, plastics, ceramics, glass, and the like. The Lid Protrusion 761 should be made of materials that adsorb negligible levels of VOCs, such as for example, glass, PTFE, and metal. The Collector Seal 742 can be made of materials that adsorb negligible levels of VOCs, such as for example, glass, metal, and PTFE. The Collector Septa 741 can be made of materials that don't adsorb much or adsorbs negligible VOCs, and can still be punctured by a needle. Examples of such materials include without limitation, PTFE and silicone.

The amount of gas in the Gas Reservoir 750 can be controlled by a number of methods, including without limitation, the size and shape of the Collector Arm 722, and the atmospheric pressure at the time of filling the Ionic Liquid Collector 710.

Figure 4:
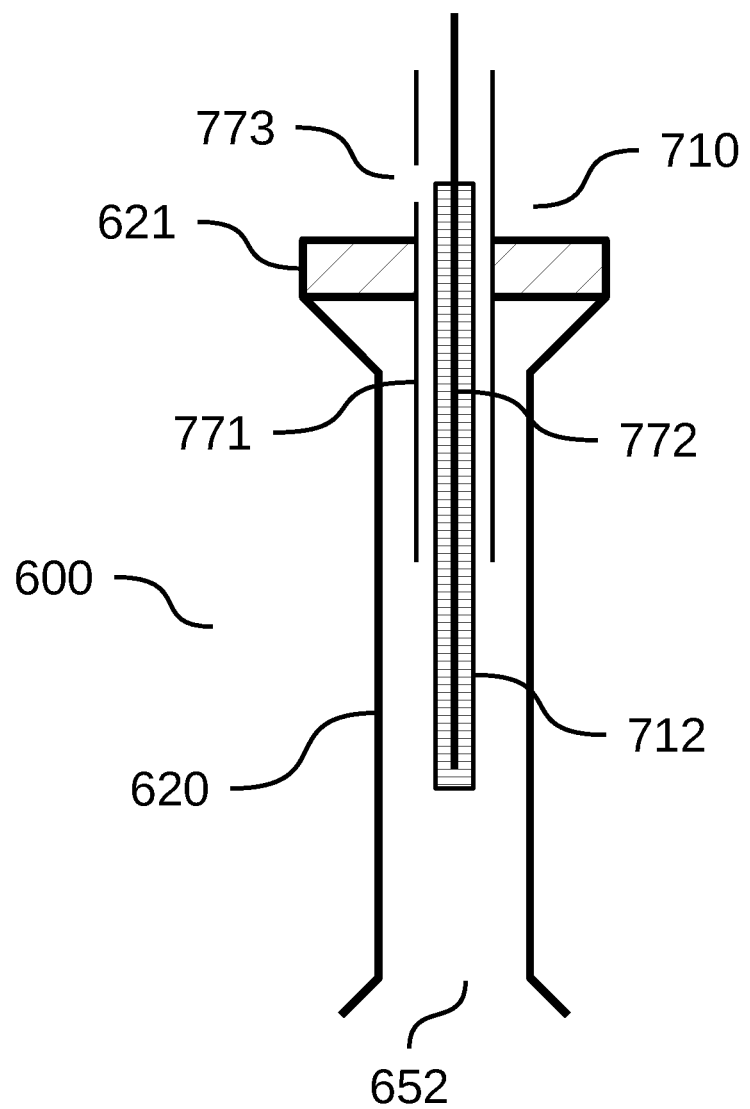
FIG. 4 is a partial sectional view of one embodiment of a Concentrator 600 and an Ionic Liquid Collector 710 for a Breath Capture Device of the present invention.

Referring now to FIG. 4, shown is a partial sectional view of one embodiment of the Concentrator 600 and Ionic Liquid Collector 710 of the present invention. The Concentrator is comprised of the Concentrator Walls 620, the Septa 621, and the Inlet 652. The Ionic Liquid Collector 710 is comprised of the Needle 771, the Ionic Liquid Support 772, the Ionic Liquid 712, and the Vent 773. In one embodiment, the Needle is open in at least one end; the Ionic Liquid Support is located within the Needle; and the Ionic Liquid is sufficiently viscous to coat the outside of the Ionic Liquid Support and not escape from the open end of the Needle. Exemplary Needles and Ionic Liquid Supports 772 for use with the present invention can be purchased commercially through Sigma Aldrich (St. Louis, Mo., USA) as an "SPME Fiber Assembly," which is reusable and comparable to the Ionic Liquid Support 772 and an "SPME Fiber Holder," which is replaceable and comparable to the Needle 773.

Still referring to FIG. 4, in application, the Ionic Liquid Collector 710 enters the Concentrator 600 by piercing the Septa 621. The breath sample enters the Concentrator 600 from the Exhaled Air Sampler via the Inlet 652. The Exhaled Air Sampler applies positive pressure thereby forcing the breath sample up between the Needle 771 and the Ionic Liquid 712. The narrow gap between the Needle and Ionic Liquid gives a high probability of a VOC molecule in the breath sample hitting the surface of the Ionic Liquid. As VOCs touch the surface of the Ionic Liquid, they tend to favorably interact and dissolve into the Ionic Liquid. The breath sample escapes the Needle through the Vent 773. It should be appreciated that by maintaining the exhaled breath sample at a warm temperature when it is inside the Concentrator 600, condensation of the VOCs on the surfaces of the Concentrator can be prevented. In contrast, by chilling the Ionic Liquid 712 until it is cold, the Ionic Liquid can help adsorb VOCs as the exhaled breath sample passes by the Ionic Liquid on the way to the Vent 773. The chilling process can be accomplished by chilling the Ionic Liquid and the Ionic Liquid Support 772 prior to injecting the Ionic Liquid Collector 710 through the Septa 621. Another way to chill the Ionic Liquid 712 is to make the Ionic Liquid Support 710 out of a conductive metal, such for example nitinol, copper, silver, aluminum or other alloys, and then chilling the Ionic Liquid Support 712, which will in turn chill the Ionic Liquid until it is cold. Chilling methods for use with the present invention include without limitation, attaching the Ionic Liquid Support to a cooling bath, a Peltier cooler, an endothermic reaction, a heat pump, and/or combinations thereof.

In one embodiment, the Ionic Liquid Collector 710 comprises a sealing mechanism that is automatically opened and closed by the Concentrator 600.

In another embodiment, the Needle 771 may be made of a metal. Examples of suitable metals for the Needle include without limitation, stainless steel, nitinol (nickel titanium), or other biologically compatible metals. The Needle 771 should be sized appropriately to work well with the analytical equipment that will perform the sample analysis. The Needle 771 may be covered by a sheath when the Ionic Liquid Collector 710 is not in use.

In a further embodiment, the Ionic Liquid Support 771 can be raised up and down through the Needle 771 to prevent the Ionic Liquid 712 from being damaged or touched when not in use. When the Concentrator 600 is in use, the Ionic Liquid Support may be adjusted up or down in the Needle to whatever position the test plan calls for. The Ionic Liquid Support 772 may be made of a metal, PDMS (polydimethylsiloxane), glass, plastics (such as polytetraethylene (PTE) and polyethylene), and combination thereof. The Concentrator Walls 620 may be made of glass, PTE, metal, or any material that does not adsorb significant amount of VOCs. As will be appreciated by those of skill in the art, it is preferential if the Concentrator Walls do not out gas VOCs. The Septa 621 may be made out any material that is suitable for being pierced with a needle, such as for example, polytetrafluoroethylene (PTFE), PTE, silicone, and combinations therefore. The Septa 621 may be replaced with a septunless seal injection port, such as those found on Gas Chromatographs. The Concentrator Walls 620 and the Septa 621 may both be designed to be replaceable.

In another embodiment, the Vent 773 ranges 10 μm to 1000 μm in size. The Vent 773 may be covered via a technical flap when the Ionic Liquid Collector 710 is not in use.

In a further embodiment, the Ionic Liquid 712 ranges from about 1 μm to about 300 μm in radius and about 1 mm to about 30 mm in length.

It is to be understood that the Ionic Liquid Collector 710 must be sized to be able to store all of the Ionic Liquid and Ionic Liquid Support 772 inside of the Ionic Liquid Collector. In FIG. 4, the entire Ionic Liquid Collector 710 is not shown. As will be appreciated by those of skill in the art, the design of the Ionic Liquid Collector will typically be tailored to the analytic machine that will perform the analysis, such as for example, Liquid Chromatography or a Gas Chromatograph.

Figure 5:
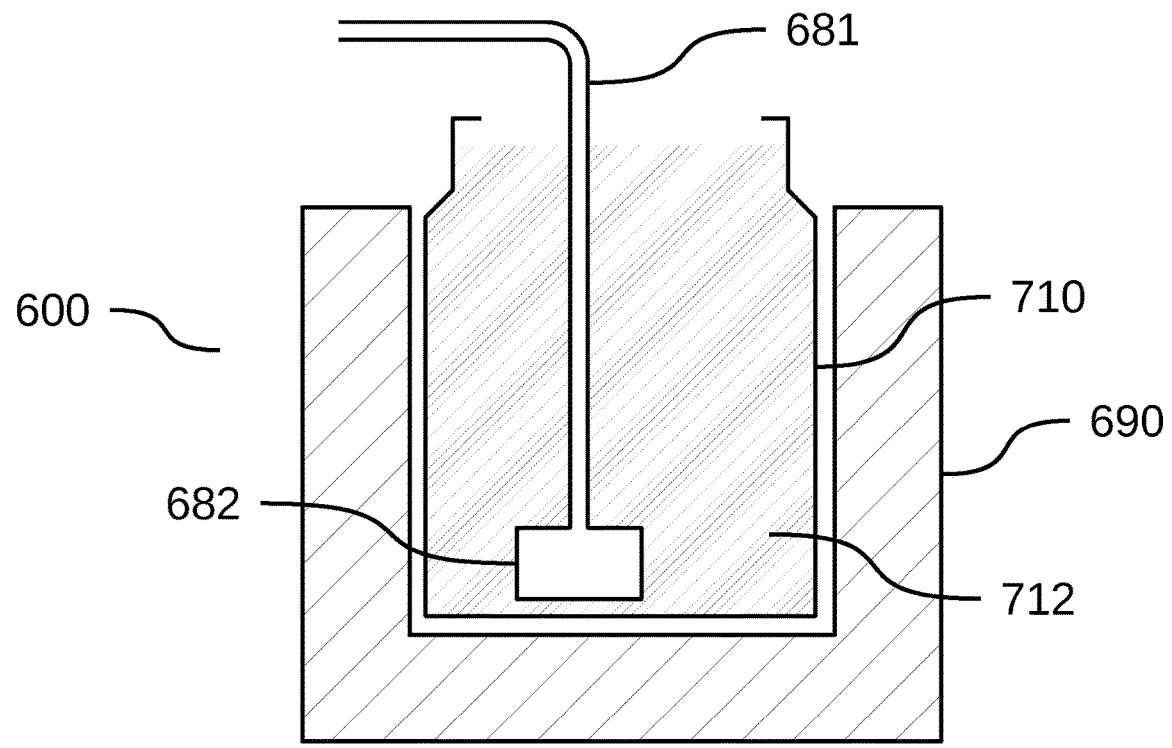
FIG. 5 is a partial sectional view of one embodiment of a Concentrator 600 and an Ionic Liquid Collector 710 for a Breath Capture Device of the present invention.

Referring now to FIG. 5, shown is a partial sectional view of one embodiment of the Concentrator 600 and Ionic Liquid Collector 710 of the present invention. The Concentrator is comprised of a Temperature Control Unit 690, a Delivery Arm 681, and a Diffuser 682. The Ionic Liquid Concentrator holds the Ionic Liquid 712.

Still referring to FIG. 5, in application, the breath sample will pass through the Delivery Arm 681 and into the Diffuser 682. The Diffuser has holes drilled into it that allow the breath sample to bubble into the Ionic Liquid 712. To increase the adsorption of VOCs into the Ionic Liquid, the Temperature Control Unit 690 keeps the Ionic liquid at an optimum temperature to adsorb the VOCs of interest.

In one embodiment, the Temperature Control Unit will have a temperature range between about −50° C. and about 150° C. The Temperature Control Unit 690 may be implemented using endothermic reactions, evaporative cooling, heat pumps, Peltier Coolers, and other temperature-regulating techniques known to those skilled in the art.

In another embodiment, the Delivery Arm 681 and Diffuser 682 are disposable and/or replaceable items.

In a further embodiment, the holes in the Diffuser 682 can be sized to maximize the diffusion rate of the VOCs into the Ionic Liquid 712. Those skilled in the art will appreciate that hole size, verses flow rate, verses viscosity of the Ionic Liquid (which is governed by temperature) allow for tuning of the adsorption rate. It should be noted that the Diffuser may contain one (1) through hundreds (100s) of holes depending on the Ionic Liquid and the targets intended to capture.

Figure 6:
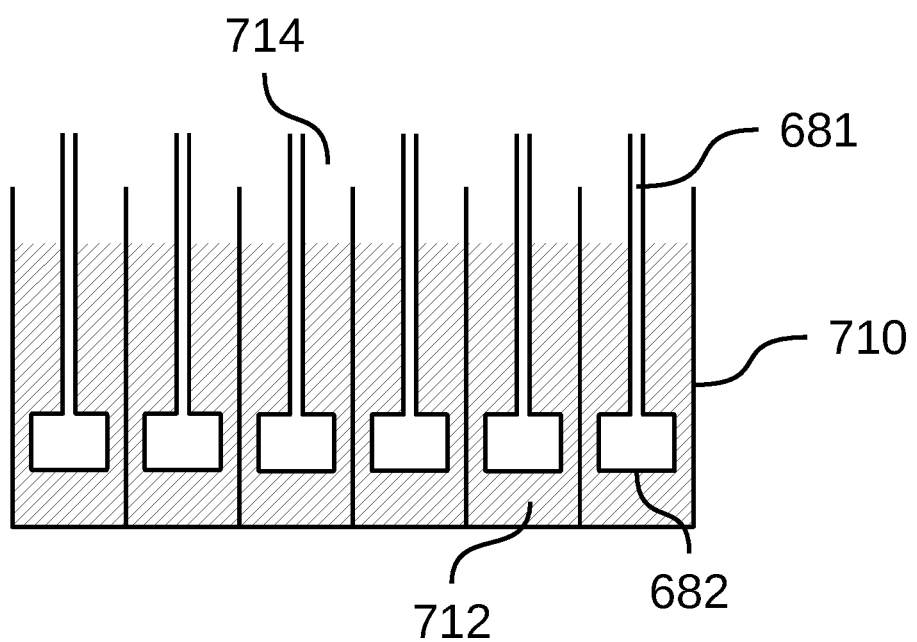
FIG. 6 is a partial sectional view of one embodiment of an Ionic Liquid Collector 710 for a Breath Capture Device of the present invention.

Referring now to FIG. 6, shown is a partial sectional view of one embodiment of a Multi-Compartment Ionic Liquid Collector 710 holding Ionic Liquid 712. The Ionic Liquid Collector is comprised of multiple Compartments 714 with each Compartment containing a Delivery Arm 681 and a Diffuser 682. Each individual Compartment of the Ionic Liquid Collector may hold a unique Ionic Liquid or the same Ionic Liquid as another Compartment. By mixing and matching the Ionic Liquid, different VOCs can be preferentially adsorbed by the Ionic Liquid in different Compartments.

Still referring to FIG. 6, a breath sample may be steered to one or all of the Ionic Liquid Containers at different times. By doing so, the location of a cancer within the lungs may be identified. In one embodiment of the invention, a baseline may be established for ambient VOCs by storing a before and/or after sample of the prevailing air in the environment in at least one Compartment 714.

Referring now to FIG. 7, shown is a partial sectional view of one embodiment of the Exhaled Air Sampler 320. The Exhaled Air Sampler is comprised of a 3-Way Value 3270, an optional Pressure Sensor 3250, an Inlet Check Valve 3240, an Outlet Check Value 3241, a Cylinder 3200, a Piston 3220, a Full Sensor 3230, an Empty Sensor 3231, a Motor 3210, an Inlet Port 3263, a Bypass Port 3262, and an Outlet Port 3261.

Still referring to FIG. 7, in application, air from the Sensor Array enters the Inlet Port 3263. The Controller can set the 3-Way Valve 3270 to send the breath sample to the Cylinder 3200 through the Inlet Check Valve 3240. The Controller can also set the 3-Way Valve to direct the air the Bypass Port 3262 and onto the Exhaust. As air enters the Cylinder 3200, the Piston 3220 moves upward until it comes in contact with the Full Sensor 3230. The Controller can then change the 3-Way Valve 3270 to send air through the Bypass Port 3262. With air in the Piston, the Motor 3210 can drive the Piston back down the Cylinder forcing the breath sample through the Outlet Check Value 3241 and out the Outlet Port 3261. The amount of time it takes to empty the Cylinder 3200 can vary between less than a second to over 10 minutes.

In one embodiment, the Controller can measure the pressure at the optional Pressure Sensor 3250 to determine if the patient is blowing.

In another embodiment, the Controller can activate the Motor 3210 to reduce the static pressure allowing the patient to easily fill the Cylinder 3200.

In a further embodiment, the Cylinder 3200 may have a heating element to keep it warm to prevent VOCs from condensing onto the walls. In addition, keeping the Cylinder at an isothermic temperature makes it possible to use materials that may expand and contract at different temperatures while still maintaining a good fit.

In another embodiment, the Cylinder 3200 and the Piston 3230 may be made of materials that do not adsorb or out gas VOCs. Examples of such materials include without limitation, glass, borosilicate glass, metal, and PTFE.

In a further embodiment, the Exhaled Air Sampler 320 may be implemented without a Piston 3200. For example, a flow meter maybe used together with the 3-Way Value 3270. When the 3-Way Valve switches to allow air to pass through to the Concentrator, the Controller can integrate the amount of air that passes the flow meter. Once a set amount of air has passed, the 3-Way Valve can shunt the exhaled air out to the Exhaust.

In another embodiment, the Cylinder 3200 may be implemented with a single input and output port.

In a further embodiment, the Inlet Check Valve 3240 and the Outlet Check Value 3241 may be implemented without electronically controlled valves. Typically the Outlet Check Value will have a higher resistance to prevent gas from escaping while the Cylinder is being filled up.

The present invention has utility in many applications, some of which are described below. It is to be understood that the applications discussed are exemplary and not meant to be limiting.

In one example, the Breath Capture Device of the present invention provides an effective way of concentrating and collecting VOCs in a consistent and reproducible manner. It will be appreciated by those of skill in the art that the ability to trap VOCs in a small Ionic Liquid Collector 710 (Examples shown in FIGS. 1-6) allows for the easy and safe transport of a VOC sample to third party labs for processing using standard shipping methods. Further, the trapping of the VOCs in the small transportable Ionic Liquid Collector 710 further allows for multiple labs to be able to analyze VOC samples from the same patient.

In another example, the Breath Capture Device provides an effective way of concentrating VOCs in exhaled air because the VOCs in the Ionic Liquid Collector 710 will be significantly higher than the VOCs in the exhaled air.

In a further example, the Breath Capture Device provides an effective way of concentrating VOCs after capture. With reference to FIGS. 2, 4, 5, and 6, if a multi-chamber Ionic Liquid Collector 710 is used it is possible to select Ionic Liquids that are preferential to the adsorption of particular VOCs.

In another example, the Breath Capture Device provides an effective way of extracting VOCs into a known gas environment. With reference to FIG. 3, when the VOCs in the Ionic Liquid Collector 710 are released from the Ionic Liquid 712 into the Gas Reservoir 750, they can be released into a known gas, such as nitrogen, helium, or gas mixtures preferential for analysis.

In a further example, the Breath Capture Device provides an effective way of concentrating the VOCs into an air sample. With reference to FIG. 3, when the VOCs in the Ionic Liquid Collector 710 are released into the Gas Reservoir 750, they can be concentrated over the VOCs in the Ionic Liquid.

In a further example, the Breath Capture Device provides an effective way of concentrating VOCs into an Ionic Liquid 712. In application, the Breath Capture Device of the present invention provides an effective way of detecting a variety of medical conditions including without limitation, lung cancer, breast cancer, prostate cancer, colon cancer, pancreatic cancer, throat cancer, small intestine bacterial overgrowth, gastric ulcers, Parkinson's, Alzheimer's, tuberculosis, autism, and throat cancer.

The Breath Capture Device of the present invention has the additional capability to be part of a complete breath analysis machine that may be designed to do a complete analysis in one location, without the need of transporting the breath sample.

It is to be understood that while the invention has been described in conjunction with the embodiments set forth above, the foregoing description as well as the examples that follow are intended to illustrate and not limit the scope of the invention. Further, it is to be understood that the embodiments and examples set forth herein are not exhaustive and that modifications and variations of the invention will be apparent to those of ordinary skill in the art without departing from the scope and spirit of the invention.

All patents and publications mentioned herein are incorporated by reference in their entireties.

EXPERIMENTAL

The following examples are set forth to provide those of ordinary skill in the art with a complete disclosure of how to make and use the features and embodiments of the invention as set forth herein.

Example 1

Application of a Multi-Compartment Liquid Collector

A device is constructed using a Multi-Compartment Ionic Liquid Collector. A subject is asked to breathe normally into the Breath Capture Device several times. During this time, the Controller determines the lung capacity of the user. After a specified number of breaths, the Controller activates the Exhaled Air Sampler to capture portions of the breath and send them to the Concentrator to be stored in different Compartments in the Ionic Liquid Container. Analysis in the lab can then look for which Compartment has the highest concentrations of biomarker, allowing the doctor to narrow down where in the Lung a disease may be localized.

Example 2

Application of a Breath Capture Device to Identify Lung Health in Different Parts of a Human Lung To test for the lung health and function of different parts of a patient's lungs, a doctor inflates a bronchial balloon catheter into the bronchi and/or bronchioles of a patient and has the patient breath through a respirator into the mouthpiece of a Breath Capture Device with a Multi-Compartment Ionic Liquid Collector. The combination of the balloon and application of the Breath Capture Device allows the doctor to capture the respiration of the patient while the doctor blocks individual major bronchi and/or bronchioles of the patient with the balloon. The touch screen interface of the Controller has a representation of a human lung with all major bronchi and bronchioles highlighted. The doctor, a nurse, or technician initiates the collection of the patient's breath samples by indicating which bronchi and/or bronchioles are blocked on the touch screen interface of the Controller. The Controller assigns a particular breath sample into one of the different compartments of the Multi-Compartment Ionic Liquid Collector and the information correlating the particular bronchi or bronchiole associated with the sample in the compartment is stored in the non-volatile storage device. By reviewing the breath sample analysis, the doctor can determine if blocking particular bronchi and/or bronchioles changes the biomarkers measured by the Breath Capture Device. By analyzing the different biomarkers, the doctor can obtain valuable information on the health and function of the different parts of the patient's lungs. The information obtained for the patient can be stored in the non-volatile storage of the Ionic Liquid Collector.

I claim:

1. A device comprising:
an intake for accepting a sample of room air;
a disposable mouthpiece for use by a human subject, wherein the disposable mouthpiece is configured for inhalation of room air through the disposable mouthpiece and exhalation of breath back into the disposable mouthpiece;
a sensor array comprising one or more sensors for measuring physical parameters in the exhaled breath;
an exhaled air sampler for capturing a pre-determined volume of air from the exhaled breath;
a concentrator for receiving the pre-determined volume of air from the exhaled air sampler, wherein the concentrator is configured to collect volatile organic compounds (VOCs) from the pre-determined volume of air; and
an ionic liquid collector comprising a container configured to hold a volume of at least one ionic liquid, receive the VOCs from the concentrator, and be removed from the device for analysis of the VOCs, wherein the VOCs are adsorbed on a surface of the at least one ionic liquid.

2. The device of claim 1, further comprising a VOC filter in communication with the intake and the disposable mouthpiece for cleaning the room air by removing VOCs from the room air sample.

3. The device of claim 2, further comprising a fan in communication with the intake and the VOC filter for moving the room air from the intake into the VOC filter.

4. The device of claim 2, wherein the VOC filter is selected from the group consisting of activated carbon filters, carbon fibers, coalescing filters, corona discharge, electrostatic filters, metal organic frameworks (MOFs), paper, silica, zeolites, and combinations thereof.

5. The device of claim 2, further comprising a one-way valve in communication with the VOC filter and the disposable mouthpiece for moving the room air from the VOC filter into the disposable mouthpiece.

6. The device of claim 5, further comprising a tracer source in communication with the VOC filter and the one-way valve.

7. The device of claim 6, wherein the tracer source is selected from the group consisting of chlorofluorocarbons (CFCs), hydrochlorofluorocarbons (HCFCs), hydrofluorocarbons (HFCs), helium, sulfur hexafluoride, and combinations thereof.

8. The device of claim 1, further comprising a one-way valve in communication with the disposable mouthpiece and the sensor array for moving the exhaled breath from the disposable mouthpiece into the sensor array.

9. The device of claim 8, further comprising a VOC source in communication with the one-way valve and the sensor array.

10. The device of claim 9, wherein the VOC source comprises one or both of crown ethers and 1,1,1,3,3-pentafluorobutane.

11. The device of claim 1, wherein the sensors on the sensor array are selected from the group consisting of electrical sensors, electrochemical sensors, optical sensors, ultrasonic sensors, semiconductor sensors, and combinations thereof.

12. The device of claim 1, wherein the physical parameters measured by the sensors on the sensor array comprise temperature, humidity, pressure, and carbon dioxide ($CO_2$) concentration.

13. The device of claim 1, further comprising an exhaust in communication with the exhaled air sampler, wherein exhaled air in excess of the pre-determined volume of air is expelled from the exhaled air sampler through the exhaust.

14. The device of claim 13, further comprising a pump in communication with the exhaled air sampler and the exhaust, wherein the pump is capable of cleaning the device.

15. The device of claim 1, wherein the exhaled air sampler further comprises a piston for collecting the pre-determined volume of air from the sensor array and injecting the predetermined volume of air into the concentrator.

16. The device of claim 15, wherein the exhaled air sampler further comprises a cylinder for housing the piston and a motor for driving the piston.

17. The device of claim 16, wherein the cylinder is configured to prevent condensation of the VOCs.

18. The device of claim 15, wherein the exhaled air sampler further comprises a pressure sensor for measuring pressure of the breath exhaled by the human subject into the device.

19. The device of claim 1, further comprising a filter in communication with the exhaled air sampler and the concentrator, wherein the filter removes moisture and other compounds from the pre-determined volume of air in the exhaled air sampler prior to the predetermined volume of air entering into the concentrator.

20. The device of claim 19, wherein the filter is made of a material selected from the group consisting of zeolites, silica gel, metal organic frameworks (MOFs), plastics, poly (dimethylsiloxane) (PDMS), fiber glass, paper, and combinations thereof.

21. The device of claim 1, wherein the concentrator comprises a VOC ionization source, wherein the VOC ionization source ionizes VOC through a mechanism selected from the group consisting of chemical ionization, electrostatic radiation, radioactivity, UV light, and combinations thereof.

22. The device of claim 1, wherein the ionic liquid collector further comprises at least one VOC trapping element for adsorbing VOCs, wherein the VOC trapping element is selected from the group consisting of activated carbon, ceramic, metal organic frameworks (MOFs), organic solvents, plastic polymers, silica, water, zeolites, and combinations thereof.

23. The device of claim 1, wherein the ionic liquid collector is a replaceable part of the device.

24. The device of claim 1, wherein the ionic liquid collector is capable of being inserted into the concentrator.

25. The device of claim 1, wherein the ionic liquid collector further comprises a needle that is injected into the concentrator, wherein the concentrator comprises a septa that is sealed and that the needle can penetrate.

26. The device of claim 25, wherein the septa is comprised of a material selected from the group consisting of polytetraethylene (PTE), polytetrafluoroethylene (PTFE), silicone, and combinations thereof.

27. The device of claim 1, wherein the concentrator is temperature controlled.

28. The device of claim 1, wherein the at least one ionic liquid in the ionic liquid collector is maintained at a temperature in the range of −50° C. to 150° C.

29. The device of claim 24, wherein the concentrator comprises a delivery arm and a diffuser, wherein the predetermined volume of air from the exhaled breath passes from the exhaled air sampler through the delivery arm to the diffuser where it is deposited in the ionic liquid collector.

30. The device of claim 1, wherein the ionic liquid collector further comprises a temperature sensor.

31. The device of claim 1, wherein the ionic liquid collector further comprises a nonvolatile storage device for storing information.

32. The device of claim 31, wherein the nonvolatile storage device is an electrically erasable programmable read-only memory (EEPROM) chip.

33. The device of claim 1, wherein the volume of the at least one ionic liquid in the ionic liquid collector is in a range of 0.03 nL to 10 mL.

34. The device of claim 1, wherein the ionic liquid collector comprises a single compartment containing a single ionic liquid.

35. The device of claim 1, wherein the ionic liquid collector comprises multiple compartments, wherein the multiple compartments contain a single ionic liquid.

36. The device of claim 1, wherein the ionic liquid collector comprises multiple compartments, wherein the multiple compartments contain different ionic liquids.

37. The device of claim 1, wherein the ionic liquid collector further comprises a collector neck comprising an air-tight sealable lid and a collector arm comprising a gas reservoir, wherein the gas reservoir allows the at least one ionic liquid to expand and contract.

38. The device of claim 1, wherein the ionic liquid collector is comprised of a material selected from the group consisting of glass, metal, polytetrafluoroethylene (PTFE), and combinations thereof.

39. The device of claim 1, further comprising a battery or power supply for powering the device.

40. The device of claim 1, further comprising a controller, wherein operation of the device is implemented through the controller.

41. The device of claim 40, wherein the controller is connected to a display and an input device.

42. The device of claim 41, wherein the controller comprises a networking interface for sending data generated by the device to third parties.

43. The device of claim 1, wherein the device is a single portable unit.

44. The device of claim 1, wherein the at least one ionic liquid is specific for diagnosis of a medical condition selected from the group consisting of lung cancer, breast cancer, prostate cancer, colon cancer, pancreatic cancer, throat cancer, small intestine bacterial overgrowth, gastric ulcers, Parkinson's, Alzheimer's, tuberculosis, autism, and combinations thereof.

* * * * *